United States Patent [19]

Tsao et al.

[11] 4,090,022
[45] * May 16, 1978

[54] POROUS CELLULOSE BEADS

[75] Inventors: George T. Tsao; Li Fu Chen, both of West Lafayette, Ind.

[73] Assignee: Purdue Research Foundation, West Lafayette, Ind.

[*] Notice: The portion of the term of this patent subsequent to Dec. 13, 1994, has been disclaimed.

[21] Appl. No.: 779,950

[22] Filed: Mar. 21, 1977

Related U.S. Application Data

[63] Continuation-in-part of Ser. No. 679,497, Apr. 22, 1976.

[51] Int. Cl.² ............... C08B 15/10; C08B 16/00
[52] U.S. Cl. .................................. 536/57; 195/63; 195/DIG. 11; 260/13; 264/13; 264/14; 264/15; 536/80; 536/98; 536/99
[58] Field of Search .............. 195/63, DIG. 11; 264/13-15; 536/57, 80, 98, 99; 260/13

[56] References Cited

U.S. PATENT DOCUMENTS

| 2,118,663 | 5/1938 | Bradshaw | 536/89 |
| 2,543,928 | 3/1951 | O'Neill et al. | 264/13 |
| 2,773,027 | 12/1956 | Powers | 264/13 |
| 2,843,583 | 7/1958 | Voris | 106/170 |
| 3,236,669 | 2/1966 | Williams | 106/311 |
| 3,251,824 | 5/1966 | Battista | 536/89 |
| 3,501,419 | 3/1970 | Bridgeford | 536/57 |
| 3,505,299 | 4/1970 | Baker et al. | 528/496 |
| 3,573,277 | 3/1971 | Grant | 536/57 |
| 3,739,049 | 6/1973 | Honjo | 264/13 |
| 3,746,621 | 7/1973 | Kondo et al. | 195/63 |
| 3,905,954 | 9/1975 | Jones et al. | 264/191 |
| 3,936,441 | 2/1976 | Holst et al. | 536/98 |
| 3,947,325 | 3/1976 | Dinelli et al. | 195/63 |

OTHER PUBLICATIONS

Tsumura et al., "Continuous Isomerization of Glucose by a Column of Glucose Isomerase," Journal of Food Science and Technology, vol. 14, No. 12, pp. 539-540 (1967).

*Primary Examiner*—Ronald W. Griffin
*Attorney, Agent, or Firm*—Cushman, Darby & Cushman

[57] ABSTRACT

Porous cellulose beads are prepared by distributing droplets of a solvent mixture containing a cellulose derivative into a precipitating solution to form porous beads which are then washed and hydrolyzed to form porous cellulose beads. The porous cellulose beads, which may be cross-linked, if desired, by suitable treatment, are useful carriers to which enzymes can be immobilized. The beads may also be used for the separation of enzymes, proteins, nucleic acids and the like, or to remove metal ions from dilute mining solutions.

20 Claims, 5 Drawing Figures

POROUS CELLULOSE BEADS

This application is a continuation-in-part of our co-pending application Ser. No. 679,497 filed Apr. 22, 1976.

BACKGROUND OF THE INVENTION

Porous cellulose beads provide a relatively lowcost, stable material possessing versatile chemical properties such that thay can be useful as a carrier for immobilized enzymes and other active biological agents.

While ordinary cellulose particles and regenerated cellulose powders meet most of the desired requirements of good carriers to which enzymes can be immobilized, they suffer from configural disadvantages which cause column reactors to become tightly packed resulting in reduction of flow and sometimes channeling, and thus insufficient contact between the immobilized enzyme and reaction fluid. The immobilization of enzymes on an insoluble carrier is a widely-accepted technique for a practical application of enzymes, avoiding the necessity of employing fresh enzymes for each desired use. Through immobilization of the enzyme, stabilization is achieved which provides for efficient enzyme use and provides for the design and operation of enzyme reactors in a continuous mode.

To a large degree, the success of an immoblized enzyme for use in practical application depends upon the properties of the carriers employed for immoblization. Accordingly, a good carrier should meet the requirements of being inexpensive and should be of such a physical shape that it is easy to be employed in reactors. In this regard, the shape of a spherical bead is particularly desirable, since it is useful in a packed bed, fluidized bed, expanded bed, stirred tank, or other common types of chemical reactor designs. Such a carrier should also have the proper physical and mechanical strength such that it will not be crushed or deformed when packed in a tall column. Crushing and deformation results in the column becoming tightly packed, thereby blocking the flow of liquid reagents through the column, thus decreasing the efficiency of the chemical reactor. Suitable carriers should also possess versatile chemical properties such that the immoblization of enzymes and other biological agents onto the carrier through ionic or chemical covalent bonding, as well as surface absorption, can be readily achieved. In this regard, the carrier should have a high capacity for forming a large number of bonds such that each unit of the carrier can immobilize large amounts of the enzyme desired. Thus, a carrier having a high degree of porosity and uniformly distributed internal void spaces is particularly desirable. Such porosity provides for good diffusion of chemical reagents or reaction products into and out of the internal void spaces of the cellulose beads. Carriers should be chemically stable, physically strong, and made of inert material which resists microbiological attack causing carrier deterioration in order to provide an immobilized enzyme system having a prolonged active life.

Currently, porous glass and porous ceramic particles are commonly employed for the immoblization of enzymes and while such particles meet most of the above requirements for an acceptable particle, they are relatively expensive. Furthermore, the number of chemical reactions which may be used for immobilization of enzymes to glass and ceramic carriers is limited.

In U.S. Pat. Nos. 3,947,325; 3,905,954; 3,573,277; 3,505,299; 3,501,419; 3,397,198; 3,296,000; 3,251,824; 3,236,669; 2,843,583; 2,773,027; 2,543,928 and 2,465,343, there is described the preparation of a variety of cellulose materials in a variety of forms, some of which are described as suitable for use in fixing biologically-active materials such as enzymes or ion-exchange groups thereto. However, these processes seem to suffer also from the disadvantage of being expensive and the products obtained generally are of an undesirable physical shape for use in such chemical reactors as packed beds and fluidized beds. In particular, the prior art fails to provide a means for producing spherical shaped cellulose beads having a uniform distribution of pores throughout the surface and a large uniformly porous internal void space. Furthermore, the cellulose particles and powders of the prior art generally are of such a small particle size that they are not suited for use in chemical reactors. In addition, the cellulose powders and particles of the prior art often have a hard surface skin which causes severe diffusional hinderance and inefficient use in chemical reactors.

In our earlier application, we describe the process of making highly porous cellulose beads of uniform porosity which were found highly suitable for immobilizing enzymes. We have found that these beads may also be useful in the purification and separation of enzymes, proteins, nucleic acids and the like. Furthermore, the beads may be useful to separate metallic ions from dilute solutions containing same.

Accordingly, the primary object of the present invention is to provide a means for preparing inexpensive, highly-porous, stable particles having versatile chemical properties whereby they may be useful as a carrier to which enzymes or other biologically-active materials can be immoblized.

A further object of the present invention is to provide a method for the transformation of cellulose derivatives into highly-porous particles having good mechanical stability such that it will provide for adequate passage of liquid therethrough when operated in packed bed reactors.

Still yet another object of the present invention is to provide a porous cellulose bead having sufficiently large surface area to provide high immobilization capacity of enzymes.

Still a further object of the present invention is to provide a porous cellulose bead having improved physical and mechanical strength so that it will not be crushed and deformed when used in chemical reactors.

Yet a further object of the invention is to provide an improved means for the purification and/or separation of enzymes, proteins, nucleic acids and the like.

Yet another object of our invention is to provide a means for the separation of metallic ions from dilute solutions containing same.

These and other objects of the present invention will be more fully apparent from the discussion set forth hereinbelow.

DESCRIPTION OF THE INVENTION

According to the present invention, a process is provided for the preparation of porous cellulose beads which are suitable for use as a carrier of enzymes and other biological agents. The invention also provides a means for the modification of the chemical and physical property of porous beads made from cellulose derivatives, as well as techniques for immobilizing enzymes and other biological active agents onto the porous beads so formed. While orginary microcrystalline cellulose and other particles made from cellulose satisfy many of the general requirements for a suitable carrier of enzymes, such particles suffer from the tendency to pack together tightly under pressure and also fail to provide sufficient porosity to attach a sufficiently-large amount of enzymes thereto. Cellulose derivatives are generally inexpensive and when treated according to our invention provide a highly-versatile material for chemical reactions being generally biologically inert. Thus, the cellulose derivative beads herein provide many desirable properties for use as a carrier of immobilized enzymes.

Our process for the modification of the physical properties of cellulose derivatives, in order to produce porous cellulose beads, involves the steps of:

a. dissolving a cellulose derivative in an inert organic, water-miscible solvent to form a solution having a density greater than that of the precipitation solution as defined hereinbelow;

b. distributing said solution in the form of droplets into a precipitation solution whereby said cellulose derivative is precipitated in the form of uniformly porous beads;

c. separating the precipitated beads from said solution;

d. washing the separated porous beads with water;

e. hydrolyzing the washed beads to convert the beads to cellulose and to increase the active sites for attachment of enzymes and other biological agents;

f. washing the hydrolyzed beads to obtain porous cellulose beads.

According to the present invention, by dissolving a cellulose derivative in a selected solvent and distributing same into a selected precipitation solution, we are able to produce cellulose beads of high uniform porosity and superior chemical and physical properties. The beads produced in accordance with the present invention are highly porous. The pores are generally uniformly distributed over the surface and throughout the interior of the bead. By proper selection of solvents and precipitation solutions, the pore size of the beads may be controlled. It is of particular advantage that in accordance with the process we are able to control both the pore size and pore distribution. With reference to FIGS. 2, 4(A) and (B), it will be seen that the pore openings are uniformly distributed over the surface of the bead and were estimated to be about 1,000 A which is a proper size for movement of enzyme and reagent molecules in the pores.

The inert organic water miscible solvent may be a single liquid or a combination of liquids. It is important that one employ a correct combination of inert organic solvent and precipitation solution in order to obtain the porous cellulose beads of desired shape and pososity. The inert organic water-miscible solvent may be a combination of liquids which together with the cellulose derivative provide a solution which when mixed with the precipitating solution results in a phase inversion whereby the cellulose derivative is coagulated in the form of a porous bead. The inert organic solvent thus contains a component (a) which is characterized as a liquid which is capable of dissolving the cellulose derivative, such as cellulose acetate, and is soluble in the precipitation solution.

A second component (b) of the solvent system is a liquid which is soluble in component (a) and also in the precipitation solution and which is present in the solvent solution in an amount sufficient that the density of the final solvent solution (together with the cellulose derivative) is sufficiently higher than the density of the precipitation solution so that upon distributing the solvent solution in the form of droplets into the precipitation solution the cellulose will coagulate and precipitate out as a porous bead of desired size and porosity. Component (b) of the solvent is used to control the surface activity of the solvent solution such that the droplets of solvent solution will maintain their shape upon contact with the precipitation solution. Component (b) also serves to control the pore size and porosity of the precipitated beads. In some instances, component (a) and component (b) may be the same. In other instances, it may be appropriate to employ one or more liquids in preparing component (a) and/or component (b).

As used herein, the term "precipitation solution" is defined as a liquid solution which is a non-solvent for the cellulose derivative and is miscible with the above inert organic, water-miscible solvent. By means of illustration, the precipitation solution may be water or an aqueous solution. The precipitation solution thus is miscible with both solvent components (a) and (b). Thus, it will be appreciated that when one dissolves the cellulose derivative in the organic solvent, and subsequently adds a drop of the resulting solvent solution to the precipitation solution, the cellulose derivative will coagulate and precipitate out due to the phase inversion which the cellulose derivative undergoes thereby forming the desired porous cellulose bead.

As will be apparent from the discussion herein, a number of variations are possible in the above-described process in preparing the desired porous cellulose beads. In addition to cellulose acetate, other cellulose derivatives may be employed as a starting material for the preparation of the porous beads, for example, cellulose nitrate and methyl cellulose. The terms "cellulose derivative" and "hydrolyzable cellulose derivative" as used herein are intended to include materials from which cellulose may be regenerated such as by means of, for example, hydrolysis or hydrogenation.

The organic solvent components (a) and (b) for the cellulose derivative can vary, but should be chemically inert to the cellulose derivative and wholly or substantially miscible with the precipitation solution. It is of prime importance that the density of the solvent solution formed by adding the cellulose derivative to the inert solvent be greater than that of the precipitation solution into which it is distributed such that when droplets of the solvent solution are distributed into the precipitation solution, the droplets will sink when the aqueous solution is not agitated. Suitable single solvents, when using an aqueous precipitation solution, include among others, for example, dimethylsulfoxide and methyl acetate. It should be understood that commercially available materials may be employed as solvent components (a) and/or (b), and that these materials may contain moisture, which in some instances has been found to be advantageous.

When employing an aqueous precipitation solution, one may suitable use as solvent component (a) a member from the group consisting of acetone, formamide a mixture of acetone and methanol or ethanol, methyl acetate, a mixture of methylene dichloride and methanol, methyl ethyl ketone and dimethyl sulfoxide. The solvent component (b) may thus be suitably chosen from a member selected from the group consisting of dimethyl sulfoxide, formamide, methyl acetate, cyclohexanone, methylene dichloride, ethylene dichloride, a mixture of methylene dichloride and methanol, and a mixture of ethylene dichloride and methanol.

A preferred solvent component (a) is acetone, but other solvents can be suitably employed, and when using an aqueous precipitation solution one may select a component (a) from the following materials (the ratio of mixtures being the minimum ratio desirable on a volume basis):

| Component (a) | Minimum Ratio (Volume) |
|---|---|
| Acetone | — |
| Acetone + Methanol | 60:40 |
| Acetone + Ethanol | 60:40 |
| Methyl acetate | — |
| Methylene dichloride + Methanol | 80:20 |
| Dimethyl Sulfoxide | — |
| Methyl Ethyl Ketone | — |
| Formamide | — |

As noted above, the primary function of component (a) is to dissolve the cellulose derivative. The addition of component (b) is necessary in order to provide a solvent solution having the requisite density such that the cellulose derivative will precipitate out in the precipitation solution. Component (b) also provides for the control of pore size and uniform porosity of the beads.

The solvent component (b) therefore provides for the desired specific gravity of the solvent solution and when employing an aqueous precipitation solution it is preferred to use dimethyl sulfoxide as component (b). As will be appreciated, in some instances component (a) and component (b) may be the same, i.e. dimethyl sulfoxide, formamide or methyl acetate when used with aqueous precipitation solutions. Various materials which may be used suitably as component (b) when employing an aqueous precipitation solution are outlined below.

| Component (b) | Minimum Ratio (Volume) |
|---|---|
| Dimethyl sulfoxide | — |
| Ethylene dichloride + methanol | 60:40 |
| Methylene dichloride + methanol | 60:40 |
| Ethylene dichloride | — |
| Methylene dichloride | — |
| Formamide | — |
| Cyclohexanone | — |

The solution of cellulose derivative and inert solvent should have a controlled cellulose derivative-to-solvent ratio since such will have an effect on the eventual porosity of the beads prepared. Generally, a small ratio (larger content of solvent) results in beads having a larger porosity. A cellulose-to-solvent (including components (a) and (b) ratio of from 1:20 and 1:3 (weight/volume) has been found suitable for preparing cellulose beads having various specific applications. Preferably, a cellulose derivative-to-solvent ratio of 1:10 to 1:6 (weight/volume) is employed to provide an easy-to-handle solution which results in porous cellulose beads of desirable properties having a void space of at least 50% by volume, preferably 75 to 95% and most suitably about 75 to 80%. Beads having a higher porosity will generally have a larger proportion of uniformly distributed internal void spaces providing less diffusion hindrance, but will be somewhat weaker in physical strength than beads of lower porosity.

The preferred precipitation solution into which the solution of cellulose derivative is to be distributed generally consists of water, but may be an aqueous solution which contains suitable amounts of non-ionic or ionic surfactants to reduce the surface tension thereof and facilitate formation of the porous beads. The precipitation solution can also suitably contain a mixture of water and methanol or ethanol (volume ratio 50:50). It is also envisioned that the precipitation may be non-aqueous so long as the cellulose derivative is insoluble therein and the necessary density requirement is met. Thus, hydrocarbon solutions may be used such as cyclohexane, hexane, decane, benzene and the like so long as they are liquid in form, possess a density less than that of the inert organic solvent and are miscible therewith. When the cellulose derivative solution is distributed by spraying via a suitable means such as a spray nozzle, the pressure drop and miscibility of the inert solvent in the aqueous solution results in a dispersion and ultimate precipitation of porous beads of the cellulose derivative.

As will be appreciated by those skilled in the art, in precipitating the cellulose beads, a sufficient amount of solvent component (b) must be present in order that the solvent containing cellulose derivative possess the requisite higher density than that of the precipitation solution. Table 1 sets forth a number of inert organic solvents for the precipitating of a cellulose derivative in an aqueous solution. The ratios set forth are the minimum needed in order to provide a solvent solution having a density greater than that of water. As can be seen, the greater the specific gravity of component (b), the less of that component is needed in order to achieve the minimum density.

TABLE 1

| Solvent Component (a) | Component (b) | Minimum Volume Ratio a:b |
|---|---|---|
| Acetone | Dimethyl sulfoxide | 70:30 |
| Acetone | Ethylene dichloride | 80:20 |
| Acetone | Methylene dichloride | 80:20 |
| Acetone | Formamide | 75:25 |
| Acetone | Cyclohexanone | 45:55 |
| Acetone | Methyl acetate | 35:65 |

After precipitation of the porous beads, cellulose is regenerated from the derivative by hydrolysis in order to create more active sites for enzyme attachment. In regenerating cellulose from its derivative after formation of the beads, one can remove the substituting groups (such as acetate from cellulose acetate) in order to regenerate all the hydroxyl groups normally present in the cellulose material. The higher the degree of regeneration, the more stability is to be found in the resulting beads. It some cases, wherein enzymes are to be immobilized on the cellulose bead carriers, it is desirable to convert the hydroxy or substituting groups into functional chemical groups, such as amino groups, which facilitate enzyme attachment.

Figure 1:
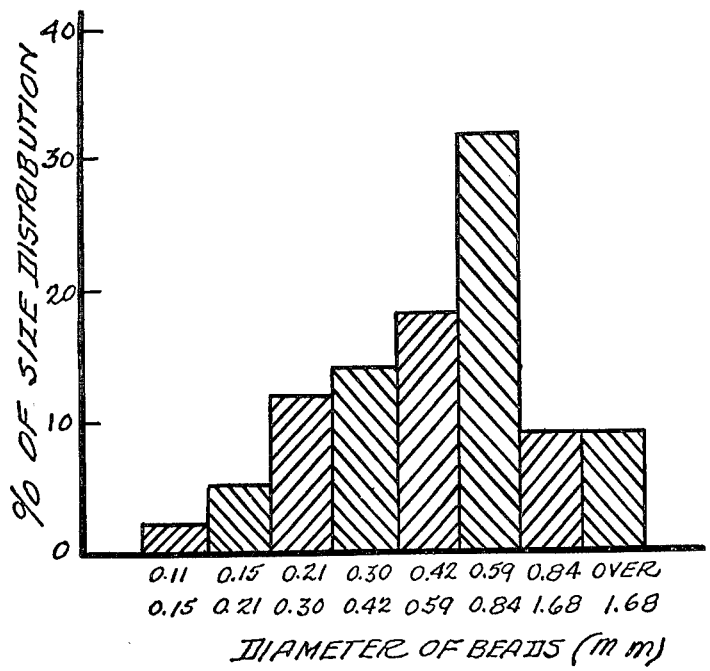
FIG. 1 is an illustration of the particle size distribution of the porous beads.

Reference is made to FIG. 1 which illustrates the size distribution of the final porous beads obtained by distributing (by spraying) a solution of cellulose derivative through a spray nozzle, according to the detailed procedure outlined hereinbelow. Beads which are either too large or too small, depending upon the intended end use, may be collected and re-dissolved in the appropriate solvent, if desired. Generally speaking, if employed in a column type chemical reactor, beads of a uniform size are preferred. The desired particle size may vary depending on the projected use of the beads, e.g. the type of enzyme to be immobilized.

Figure 2:
FIG. 2 is a scanning electromicrograph of a porous cellulose bead.
Figure 4A:
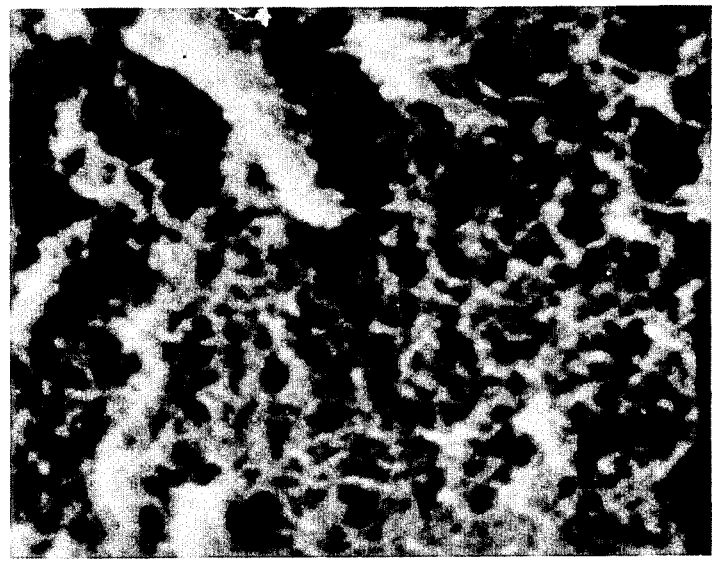
FIG. 4(A) is a scanning electron micrograph of the surface of a porous cellulose bead (20,000x).
Figure 4B:
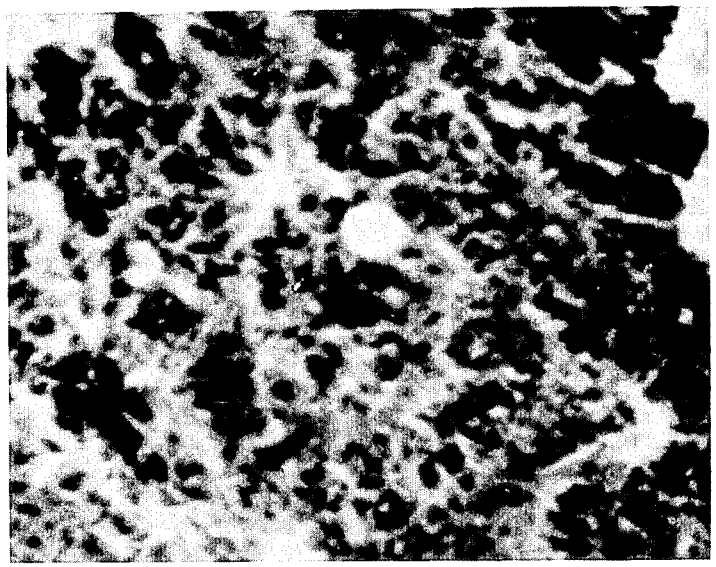
FIG. 4(B) is a scanning electron micrograph of the interior of a porous cellulose bead (20,000x).

The porous cellulose beads prepared by the process described above generally have a very high porosity and a controlled pore size ranging from 0.05 to 30 microns. When a cellulose-to-solvent ratio of 1:10 (weight/volume) is used in preparing the cellulose/solvent solution, the final beads formed have a high porosity of about 90% void. A scanning electromicrograph of a porous cellulose bead prepared by the process is shown in FIGS. 2, 4(A) and 4(B). From these views, one can observe several important features of the beads produced. Firstly, it can be seen that the beads are generally spherical in shape and porous openings are uniformly distributed over the surface of the beads. For most applications, this is desirable because it can provide an immobilized enzyme catalyst of uniform activity. The void phase of the cellulose beads is continuous. This is a desirable feature because a discontinuous, discrete "bubble" would result in useless and nonaccessible dead space in an immobilized enzyme system. Thirdly, there is no hard "skin" at the bead surface. A hard skin will cause serious diffusional hindrance. Finally, the pore sizes are quite uniform. As a result, all of the interior surface area of the internal void spaces of the beads will be accessible for enzyme immobilization and for enzyme catalyzed reactions. Both the high porosity and other noted features have made the porous cellulose beads of this invention uniquely suited for use in immobilization of enzymes and other biologically-active agents.

An important property of an enzyme carrier is the pressure drop it causes at various liquid flow rates through an enzyme reactor containing the carrier. For example, DEAE-cellulose is currently used in industry and an enzyme carrier for the conversion of glucose into fructose. For DEAE-cellulose, the pressure drop is very high and consequently only shallow beds can be used to obtain a reasonable rate of fluid flow. The pressure drop characteristics of the porous cellulose beads of this invention in a packed column operation is shown by Curve A in FIG. 3. The nominal linear flow velocity is calculated by dividing the volumetric flow rate of the feed liquid to the column by the column cross-sectional area. In practical operations, the nominal linear flow velocity in industrial column reactors will be less than 0.5 cm/sec. For example, with a reactor column of two feet (60.96 cm) inside diameter, a linear velocity of 0.5 cm/sec is equivalent to a volumetric flow rate of 1389 gal/hr (5254 liters/hr). In a typical industrial operation for producing fructose from glucose, the sugar concentration in the feed is about 5 lb. sugar/gallon. The above flow rate will yield more than 60 million pounds of the product per 2 feet column per year. Because of the residence time requirement of the enzymatic reaction, the linear flow rate is usually less than 0.5 cm/sec.

Therefore, it can be seen that the porous cellulose beads of this invention do not pose any serious engineering problems with regard to pressure drop, when used in column type chemical reactors as a carrier to which enzymes and other biologically-active agents can be immoblized. When the porous cellulose beads, after proper derivatization, are used for other potential applications (e.g. removal of tannin from fruit juice, wine or beer as well as metallic ions from dilute solutions) the liquid flow rate through a reactor column could be much larger than that of 0.5 cm/sec cited here.

Figure 3:
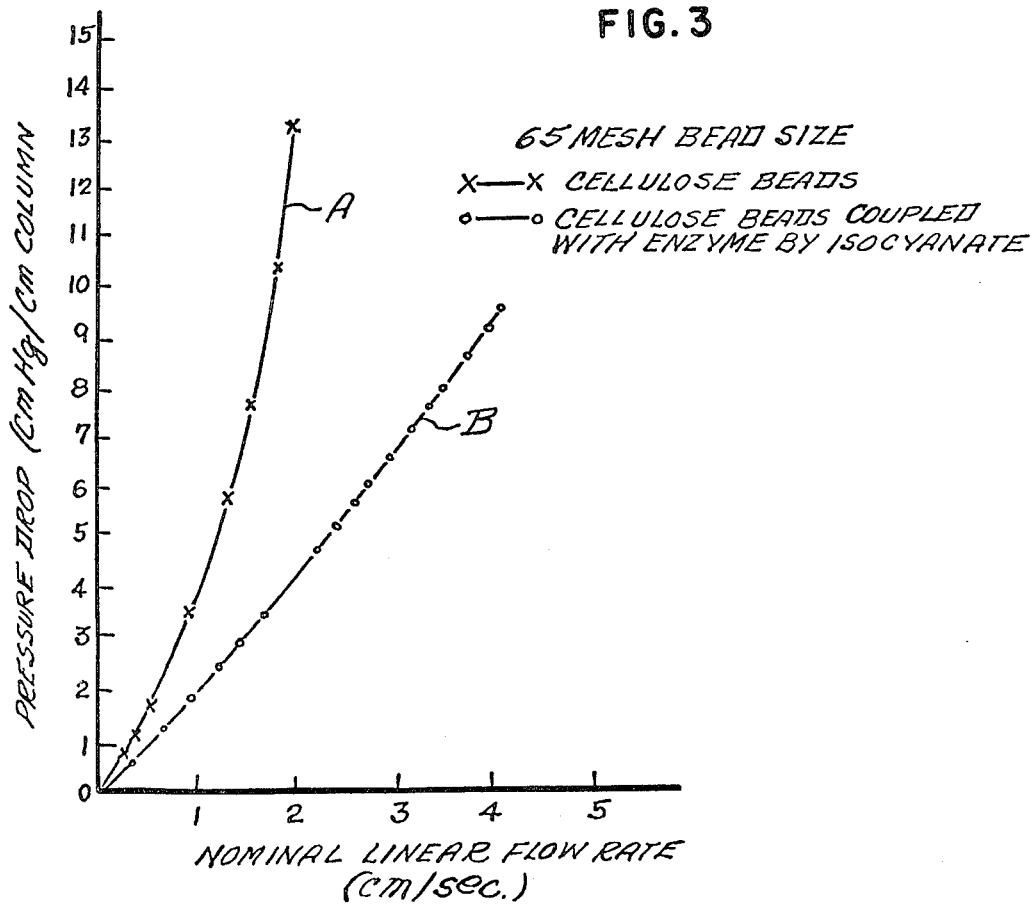
FIG. 3 is a plot of the pressure-drop-characteristics of the porous cellulose beads.

The flow characteristics and other physical and mechanical properties of the porous cellulose beads can be improved by cross-linking with bi- and/or multi-functional compounds. Curve B in FIG. 3 shows the pressure drop requirement of the porous cellulose beads after the treatment with tolylene-2, 4-diisocyanate and enzyme immobilization. Above a nominal linear velocity of 2 cm/sec, the untreated cellulose beads (Curve A) become compressed and deformed considerably, resulting in a drastic increase of the pressure drop. Curve B concaves upward only slightly indicating little deformation, if any, of the treated beads.

Treatment of the porous cellulose beads with a cross-linking agent, either before or after hydrolysis of the beads, results in an increase of their physical strength. Attachment of enzymes onto the beads will also increase their physical strength. After treatment with, for example, a diisocyanate (e.g., tolylene-2, 4-diisocyanate or hexamethylene diisocyanate), the beads in fact become quite rigid and strong. Cross-linking with epichlorohydrin also improves the physical properties of the porous cellulose beads. The chemistry of cross-linking of polysaccharides, including cellulose and starch, is a well-developed branch of physical science. Other suitable cross-linking agents among others include formaldehyde in hydrochloric acid solution or glutaraldehyde. Many other carbohydrate cross-linking agents are well known, as shown, for example, by Jones et al, U.S. Pat. No. 3,905,954.

In general, the porous beads of the present invention are prepared according to the following steps:

a. a hydrolyzable form of cellulose is dissolved in an inert organic water-miscible solvent in a controlled ratio of cellulose derivative-to-solvent which is generally in the range of 1:20 to 1:3 (weight:volume) to produce a solvent solution. The solvent should be wholly or substantially miscible with the precipitation solution and the density of the solvent solution should be sufficient that upon contact with the precipitation solution, the solvent becomes readily miscible with the precipitation solution and the cellulose derivative precipitates therein.

b. a solvent solution is distributed (e.g., by spraying) in the form of droplets into a precipitation solution Upon contact with the precipitation solution, which may contain a surfactant, the solvent is dispersed within the solution media and porous beads of the cellulose material form as they coagulate and precipitate to the bottom of the tank holding the precipitation solution. The cellulose derivative solution may suitably be sprayed under pressure through an atomizing nozzle into a precipitation solution bath. If desired, the bath may be agitated to enhance the formation of the beads.

c. the precipitated beads, after being washed, are then hydrolyzed in order to regenerate cellulose, thereby providing a porous cellulose bead having active sites for enzyme attachment. If desired, in order to increase the stability of the porous beads or provide suitable reaction sites, one can chemically modify the beads in a number of ways. For example, the beads may be cross-linked in order to provide greater stability and increased physical strength. Also one can chemically substitute either positively-charged or negatively-charged groups to alter the surface-absorption properties of the cellulose bead. The cellulose itself is generally hydrophilic and, thus, by altering the reaction sites thereof, one can alter its hydrophilic properties.

The present invention further provides for a method by which enzymes and other biological active agents may be immobilized by attachment onto the porous cellulose beads described hereinbefore. For example, one may convert porous cellulose beads, as described above, to diethylaminoethyl (DEAE) cellulose by reacting said beads with N,N-diethyl 2-chloroethylamine hydrochloride in a conventional manner. Beads so obtained contain DEAE-cellulose and were successfully used to attach glucose isomerase, derived from a streptomyces culture. We have also employed a procedure involving cyanogen bromide to immobilize the glucose isomerase.

Another procedure for enzyme immobilization on the porous cellulose beads involves the use of tolylene-2,4-diisocyanate. Diisocyanate was employed to cross-link cellulose to improve the physical strength of the porous beads. However, we have found that the porous cellulose beads of the present invention when treated with diisocyanate, can immobilize enzymes on the surface thereof by simply mixing the diisocyanate-treated beads together with an enzyme solution. For example, when glucoamylase was used, the diisocyanate beads attached more than 1000 international units of the enzyme per gram of dry beads. While not wishing to be limited in any way by the following theory, it appears that when dry porous cellulose beads are in dry acetone with tolylene-2,4-diisocyanate in the presence of a catalyst (for example, triethylamine), a considerable degree of crosslinking occurs between cellulose molecules in light of the improved physical strength of the beads. After a sufficient length of time for reaction, the beads were washed with dry acetone to remove free diisocyanate residues. The cellulose beads appear to possess a large number of attached isocyanate groups. Upon mixing the treated beads with an aqueous enzyme solution, enzyme molecules appear to be covalently bonded to the cellulose beads through the isocyanate groups. It has also been found that washing the treated beads with water results in converting isocyanate groups to amino groups. In such a manner, we were successful in immobilizing an enzyme, glucoamylase, to the amino cellulose beads with glutaraldehyde, an agent well known for its capability of reacting and cross-linking amino groups (on the beads and the enzyme).

The porous celulose beads produced in accordance with the present invention also find use in the separation and purification of enzymes, proteins, nucleic acids and the like. The porous cellulose beads produced in accordance with the process of the present invention may be derivatized to produce DEAE-porous cellulose beads which possess excellent flow properties and yet are able to efffectively separate enzymes, proteins, nucleic acids and the like as effectively as current commercial products according to the technique known as column chromatography.

Also, one may derivatize the porous cellulose beads of the present invention (in situ) with groups other than DEAE. Thus, the porous cellulose beads of the present invention are applicable for a wide variety of specific applications. For example, one can attach a specific functional group to the porous cellulose beads and the then derivatized beads may be used to, for example, remove tannin from fruit juice by passing the juice through a bed of the derivatized porous cellulose beads with protein.

In a similar fashion, one may remove metallic ions from dilute solutions containing same. Such a method would provide for the recovery of valuable metallic ions (i.e., copper ions and gold ions) from dilute mining solutions, and would find particular applicability to current solution mining techniques whereby metals are extracted from ores by acid solutions.

The following examples are offered to more fully describe the invention, but are not to be construed as limiting the scope thereof:

EXAMPLE I

Fifty grams of cellulose acetate (Visc 3 from Eastman Kodak Chemicals) were dissolved in 400 ml of solvent A (composed of acetone and dimethyl sulfoxide in a volume ratio of 6-to-4) to form a 12.5% (weight-/volume) solution. With a spray gun (paint sprayer from Sears Roebuck & Co.), the cellulose solution was then sprayed at an air pressure of 20 psi as fine droplets into a water tank containing 40 gallons of water and four drops of common household detergent. Upon contacting the surface of the water, the cellulose acetate droplets coagulate into porous beads and sink to the bottom. The porous beads were then collected and washed. The washed beads were then deacetylated with about a 0.15 N of sodium hydroxide overnight at room temperature. The deacetylated beads were then washed and suction-dried, yielding a porous cellulose bead having a void space greater than 50% by volume ready for use in enzyme immobilization. FIG. 1 illustrates the size distribution of the porous beads obtained. Electron micrographs revealed that the beads were generally spherical, with the interior and surface thereof having the same structure. The pore sizes were quite uniform and the pores were distributed uniformly throughout the entire bead as illustrated in FIGS. 2, 4(A) and 4(B). The pore size of the beads was determined from scanning electron micrographs. The scanning micrographing requires dry samples and since the drying of the beads in air results in a size shrinkage, the beads were dried by the critical point technique with liquid carbon dioxide. The pore size was determined to be about 1000 A.

EXAMPLE II

Using a 10% (weight/volume) cellulose acetate solution in solvent A, according to the process of Example I, porous beads were also formed and were suitable for use in enzyme immobilization.

EXAMPLE III

A 10% (weight/volume) cellulose acetate (Visc 3 from Eastman Kodak Chemicals) solution was prepared in solvent B (acetone and formamide in a volume ration of 7-to-3). The cellulose acetate solution was then sprayed and hydrolyzed according to the procedure in Example I above. Highly porous cellulose beads were obtained having a void space greater than 50% by volume.

EXAMPLE IV

The procedures outlined in Example II, above, were repeated using a solution prepared with cellulose acetate of Visc 45 type (available from Eastman Kodak Chemicals). Porous beads were also obtained having excellent properties for enzyme immobilization.

EXAMPLE V

The procedures outlined in Example II, above, were carried out using a 10% weight/volume solution of cellulose triacetate (available from Eastman Kodak Chemicals) in solvent A. The beads resulting therefrom exhibited excellent porosity for enzyme immobilization. As we have noted, cellulose can be used as a supporting material for the immobilization of enzymes and other biologically active agents. Many workers have chosen cellulose as a support because cellulose is inexpensive, chemically stable, and it is resistant to microbiological contamination. Also, cellulose has three hydroxyl groups on each anhydro-glucose unit which provides high versatility as well as large capacity for the immobilization of a desired substance.

The major disadvantage of using cellulose as a supporting material is that cellulose has a fibrous shape and lacks the necessary mechanical strength. Reactors packed with cellulose have poor flow properties, develop severely high pressure drop, and sometimes channelling. To overcome these problems, we prepared cellulose into a bead form according to the present invention which exhibited a better mechanical strength and provided enhanced flow properties than prior materials. However, since the structure of our cellulose beads differs from that of regular cellulose, the loading of enzymes and stability of the immobilized enzymes may differ from that with regular cellulose. The chemistry involved in the preparation of immobilized enzymes not only affects the loading and stability of the enzyme on the cellulose beads, but also affects the mechanical strength of the cellulose beads. Any chemical procedures for immobilization of enxymes, which increase mechanical strength of cellulose beads, would improve the flow properties in a reactor, as will be apparent from the examples.

EXAMPLE VI

One gram of porous cellulose beads, produced according to Example I, was dispersed in 15 ml water which was adjusted to pH 11.5 with sodium hydroxide and kept at a constant temperature of 20° C. One gram of cyanogen bromide was added to this dispersion. The pH was maintained at 11.5 with 1 N NaOH. After 15 minutes, the beads were washed with a phosphate buffer (0.1 M) at pH = 7.0 and 0° C. Fifteen ml of glucoamylase solution (30 mg/ml) were then added to the beads. The mixture was left overnight. The beads so prepared contained 1830 units of enzyme activity per gram dry weight of cellulose bead at 60° C. using 5% maltose as substrate. One unit of enzyme activity is defined to be that which produces one micromole of product per minute.

EXAMPLE VII

Porous cellulose beads (0.2 gm), obtained as in Example I, were dispersed in 5 ml acetone. 0.2 ml triethylamine was added to the dispersion as was 0.2 ml of tolylene-2,4-diisocyanate. After 30 minutes, the beads were washed with acetone and then an acetate buffer at pH 4.75. Five ml of glucoamylase solution (25 mg/ml) were added. The enzyme was thereby immobilized on the beads with an activity of 2,000 units/gm cellulose beads.

EXAMPLE VIII

Two hundred mg glucose isomerase in maleic acid buffer solution was immobilized onto 2 gm of cellulose beads by the same procedure as described in Example VII. The cellulose beads contained 90 units of enzyme activity per gm of cellulose beads at 60° C. using 9% fructose as the substrate.

EXAMPLE IX

Three hundred mg of invertase in 5 ml of acetate buffer were immobilized onto 0.5 gm of porous cellulose beads using the procedure described in Example VII. The cellulose beads contained 3000 units activity per gm of cellulose used.

EXAMPLE X

Fifty mg of lactase in phosphate buffer (pH = 7.0) were immobilized onto 0.5 gm cellulose beads using the procedure, described in Example VI. The resulting cellulose beads contained about 80 units enzyme activity per gm of cellulose beads at 30° C. using 1% lactose as substrate.

EXAMPLE XI

Five hundred mg of glucose isomerase were dissolved in 150 ml maleic acid buffer (0.01 M, pH = 5.5). The enzyme soltuion was pumped through 5 gm porous crosslinked cellulose beads prepared as described in Example XVI. The DEAE cellulose beads thus contained 100 units of enzyme activity per gm of beads.

EXAMPLE XII

One-quarter gm of porous cellulose beads, produced in accordance with Example I, was soaked in 3% of glutaraldehyde and 0.1 M $MgCl_2$. After drying, using vacuum suction on a Buchner funnel, the samples were heated at 80° C. for 30 minutes. Five ml of glucoamylase (25 mg/ml) were added to the beads. After standing overnight, the beads thus prepared contained about 200 units of enzyme activity per gm of dry cellulose beads.

EXAMPLE XIII

One gm of porous cellulose beads was cyanoethylated with 10 ml acrylonitrile (C = CC≡N) at 50° C. The so-treated cellulose beads were then treated with hydorxylamine at a pH 6.5 - 6.7 at 50° - 100° C. for 4 hours. The resulting modified porous bead product contained

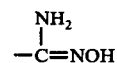

groups and is suitable for absorbing heavy ions such as ferric, ferrous, and cupric.

EXAMPLE XIV

A suspension of 2.5 gm porous cellulose beads was treated with 2.5 ml hexamethylene diisocyanate and triethylamine, followed by hydrolysis in water. The product was then treated with 50 ml of 0.5 M 0-methyl iso-urea at pH 5. The product obtained has the following funtional group:

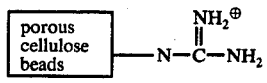

which is useful as an anionic ion exchanger.

EXAMPLE XV

Five grams of porous cellulose beads, obtained according to Example I, were added to 100 ml of 36% formaldehyde and 200 ml of 37% hydrochloric acid. After standing for 1½ hours at room temperature, the beads were filtered and subsequently washed with water and 0.2% sodium carbonate solution. The beads were then dried at 75 to 80° C. The resulting cross-linked porous cellulose beads exhibited strong physical strength.

EXAMPLE XVI

Three grams of porous cellulose beads were cross-linked by formaldehyde according to the process in Example XV. The beads were then treated with 3 grams of 2-chlorotriethylamine. After heating the mixture for a period of 35 minutes at a temperature of 80 to 85° C., the beads were then washed sequentially with sodium chloride, sodium hydroxide, hydrochloric acid, water and ethanol. The cross-linked porous DEAE cellulose beads so obtained exhibited excellent porosity having a void space greater than 50% by volume.

EXAMPLE XVII

A dispersion was formed of 0.5 grams porous cellulose beads in 5 ml of 0.2 N sodium hydroxide and 5 ml epichlorohydrin. The dispersion was then heated for several minutes to a temperature of 80° C. Subsequently, the beads were washed and the cross-linked porous beads so treated exhibited greater strength than the porous cellulose beads prior to crosslinking. Wet cellulose beads, obtained according to the procedure of Example I, were washed in acetone. The washed beads were then suspended in dry acetone containing 0.6 ml of triethylamine for each gram of cellulose. Tolylene-2,4-diisocyanate, in an amount of 1.6 ml per gram of cellulose beads was added to the suspension at 0° C. After a period of 30 minutes, the beads were washed with dry acetone and subsequently filtered. The resulting porous cellulose beads contain isocyanate-reactive groups which could then be hydrolyzed to an amino group by the addition of water.

EXAMPLE XVIII

Two tenths g of the cellulose beads produced as in Example I were suspended in 10 ml of distilled water, the pH was adjusted to 11.5 by the addition of 1 N NaOH at 20° C. Two tenths g of CNBr was added to the cellulose beads suspension, a small portion at a time, and the pH was maintained by an auto-titratometer with 1 N NaOH. After 20 minutes the beads were washed with ice cold distilled water and an appropriate buffer solution. Enzymes dissolved in a proper buffer solution were added to the washed cellulose beads. Cellulose (Solka floc) used in this method was mercerized with 18% (w/v) NaOH for 4 hours then washed with distilled water.

EXAMPLE XIX

Two g of suction dried cellulose beads of Example I were washed with acetone to remove moisture and were suspended in 10 ml of acetone. One tenth ml of triethylamine or dibutyltin diacetate were added as catalyst. One tenth ml of tolylene-2,4-diisocyanate or hexamethylene diisocyanate were added to the cellulose bead suspension. After 45 minutes of reaction at ambient temperature, the cellulose beads were washed with acetone to remove excess diisocyanate and water was then used to wash the cellulose beads to remove acetone. Enzymes dissolved in an appropriate buffer solution were added to the cellulose beads. The cellulose beads were stored at 4° C overnight.

EXAMPLE XX

Aryl diisocyanate was attached to cellulose beads as described in Example XIX. Before the enzyme solution was added, the cellulose beads were suspended in distilled water. One tenth ml of triethylamine was added to catalyze the reaction between isocyanate and water to form aryl amine cellulose beads. The arylamine derivative was then diazotized with $NaNO_2$ in HCl. Enzymes suspended in a proper buffer solution were then attached to the cellulose beads.

EXAMPLE XXI

Diisocyanate attached on the cellulose according to Example XIX reacts with water to form amino group with or without a tertiary amine as catalyst. Glutaraldehyde is used to couple the enzyme onto the cellulose beads by crosslinking amino groups on enzymes and on cellulose beads.

EXAMPLE XXII

Two g of suction-dried beads produced in accordance with Example I were suspended in 10 ml of 3% glutaraldehyde which was 0.1 M in Mg $Cl_2$. The suspension was heated at 100° C for 30 minutes. The cellulose beads were then washed with distilled water. Enzymes dissolved in an appropriate buffer solution were added to the cellulose beads. The reaction was allowed to continue overnight at 4° C.

EXAMPLE XXIII

One g of cellulose beads produced according to the procedure of Example I was refluxed with 10 ml of 10% 3-aminopropyltriethoxysilane in toluene for 4 hours. The cellulose beads were then filtered and washed with acetone. 2.5% (w/v) glutaraldehyde solution in 0.1 M phosphate buffer pH = 7.0) was added to the cellulose beads at ambient temperature for one hour with occasional stirring. The cellulose beads were then washed thoroughly with water and an appropriate buffer solution. Enzymes dissolved in an appropriate buffer solution were added to the cellulose beads. The reaction was allowed to continue overnight at 4° C.

EXAMPLE XXIV

Porous cellulose beads produced in accordance with the procedure of Example I were first cross-linked by 36% formaldehyde and 37% HCl with a volume ratio of 5 to 1. The crosslinked cellulose beads (5 g dry weight) were suspended in 50 ml of cold 1.5 N NaOH solution. Six g of 2-Chlorotriethylamine hydrochloride were added to the cellulose beads. The mixture was then heated at 80° – 85° C for 35 minutes. The mixture was cooled in an ice bath and filtered. The cellulose beads were washed with 500 ml of 2M NaCl and then were washed with 200 ml of 1N NaOH and 200 ml of 1N NaOH, alternately for three times. After washing with another 200 ml of 1N NaOH, the cellulose beads were washed with distilled water until the pH of washing water became neutral. The reaction with 2-chlorotriethylamine hydrochloride was repeated again for a higher degree of substitution. Enzymes dissolved in an appropriate buffer were added to the cellulose beads for overnight at 4° C.

EXAMPLE XXV

Hexamethylene diisocyanate was attached to cellulose beads as described in Example XIV and then the isocyanate groups were hydrolized to form amino group as described in Example XX. O-methyl isourea was added to the cellulose beads to incorporate the guanidino function into the derivatized beads.

Examples XVIII through XXIII provide for immobilization of enzymes by covalent bonding, whereas Examples XXIV and XXV utilize ionic adsorption. Glucoamylase, glucose isomerase and invertase were loaded onto various of the beads of Examples XVIII to XXV and the amount of enzyme loading measured.

The enzymes immobilized by covalent bonding were washed with 2M NaCl solution to remove the absorbed enzymes. Some properties of the immobilized enzymes are shown in Table 2. It indicates that the same chemistry used for regular cellulose can also be used for cellulose beads. The fact that cellulose beads have higher enzyme loading capacity than regular cellulose may indicate a larger surface area in the porous cellulose beads.

EXAMPLE XXVI

Protein and enzymes may be separated and purified according to the following procedure. 2 gm of glucose isomerase (Strep. albus obtained from Miles Laboratory) was suspended in 20 ml of 0.01M phosphate buffer (pH = 7.0) and the suspension centrifuged. The supernatant was added to a column of DEAE-porous cellulose beads produced according to Example XVI. The bed volume was 30 ml and the column diameter 1.5 cm. The colume was washed with 0.01M phosphate buffer (pH = 7.0). The column was eluded with NaCl gradient solution in 0.01 M phosphate buffer. Glucose isomerase began to elude out of the column in the NaCl fractions with concentrations ranging from 0.25 to 0.45 M.

Table 2

| Enzyme Loading on Porous Cellulose Beads | | | | |
|---|---|---|---|---|
| Enzymes | Method of Immobilization Example | Enzyme loading on cellulose, IU*/g (calculated from initial reaction rate) | | Assay conditions |
| | | regular cellulose | Porous cellulose beads | |
| | XVIII | 820 | 1,8000 | 10% Maltose, 60° C |
| | XIX | | 550 | " |
| Glucoamylase (A. Oryzae) | XX | | 275 | 10% Maltose, 40° C |
| | XXI | | 530 | 5% Maltose, 60° C |
| | XXII | 80 | 190 | 10% Maltose, 60° C |
| | XXIII | | 200 | " |
| Glucoamylase (A. Niger) | XXIV | 3,000 | 9,000 | " |
| | XXV | | 1,000 | " |
| | XIX | | 90 | 0.5M Fructose, 60° C |
| Glucose Isomerase (Strep. albus) | xXIV | | 300 | " |
| | XXV | | 160 | " |
| Invertase (Candida utilis) | XIX | | 1,140 | 0.125M Sucrose,45° C |
| | XXIV | | 2,000 | " |
| | XXV | | 1,840 | " |

*IU - international units

EXAMPLE XXVII

The porous cellulose beads of Example XIII are added to a 0.05 M sodium acetate solution (pH = 5.2) which contains 1,600 ppm of cupric ion. After one hour, the cellulose beads picked up 6.3% cupric ion by weight of the beads.

We have also found that when the porous cellulose beads of the present invention are dried and/or heated, e.g. at 100° C prior to use, the resulting beads exhibit an increased physical strength.

The invention, in its broadest aspects, is not limited to the specific details shown and described, but departures may be made from such details within the scope of the accompanying claims without departing from the principles of the invention. Furthermore, the invention may comprise, consist, or consist essentially, of the hereinbefore-recited materials and steps.

We claim:

1. A process for the preparation of porous cellulose beads suitable for use as a carrier of enzymes and other biological agents which comprises the steps of:
   a. dissolving a hydrolyzable cellulose derivative in an inert organic, water-miscible solvent to form a solution having a density greater than that of a precipitation solution the cellulose derivative to solvent ratio ranging from 1:20 to 1:3 weight-/volume;
   b. distributing said solution in the form of droplets into a precipitation solution whereby said cellulose derivative is precipitated in the form of uniformly porous beads;
   c. separating the precipitated beads from said solution;
   d. washing the separated porous beads with water;
   e. hydrolyzing the washed beads to convert the beads to cellulose and to increase the active sites for attachment of enzymes and other biological agents;
   f. washing the hydrolyzed beads to obtain porous cellulose beads having a uniformly distributed void space greater than 50% by volume.

2. A process according to claim 1 wherein distributing is accomplished by spraying.

3. A process according to claim 1 wherein said precipitation solution is selected from the group consisting of water, hexane, cyclohexane, octane, benzene and mixtures of water and ethanol or methanol.

4. A process according to claim 3 wherein said precipitation solution is water.

5. A process according to claim 1 wherein said cellulose derivative is cellulose acetate and hydrolysis is carried out in a caustic solution.

6. A process according to claim 1 wherein said solvent is a mixture of:

a. a member from the group consisting of acetone, a mixture of acetone and methanol or ethanol, methyl acetate, a mixture of methylene dichloride and methanol, methyl ethyl ketone, formamide and dimethyl sulfoxide; and b. a member from the group consisting of dimethyl sulfoxide, formamide, methyl acetate, cyclohexanone, methylene dichloride, ethylene dichloride, a mixture of methylene dichloride and methanol, and a mixture of ethylene dichloride and methanol.

7. A process according to claim 6 wherein said solvent is dimethyl sulfoxide, formamide or methyl acetate.

8. A process according to claim 1 wherein the void space of said beads is from about 75 to 95%.

9. A process according to claim 1 wherein said porous cellulose beads are cross-linked with at least one cross-linking agent to obtain cross-linked porous cellulose beads.

10. A process according to claim 9 wherein said beads are cross-linked prior to being hydrolyzed.

11. A process according to claim 9 wherein said beads are cross-linked after being hydrolyzed.

12. A process according to claim 9 wherein said cross-linking agent is a diisocyanate.

13. A process according to claim 12 wherein said diisocyanate is tolylene-2,4-diisocyanate or hexamethylene diisocyanate.

14. A process according to claim 9 wherein said cross-linking agent is epichlorohydrin in a sodium hydroxide solution.

15. A process according to claim 9 wherein said cross-linking agent is formaldehyde in a hydrochloric acid solution.

16. A process according to claim 9 wherein said cross-linking agent is glutaraldehyde.

17. Porous cellulose beads produced according to the process of claim 1.

18. Porous cross-linked cellulose beads produced according to the method of claim 9.

19. A method for the removal of metallic ions from a dilute solution containing said ions which comprises contacting the dilute solution with the porous cellulose beads of claim 17, said beads being further characterized by the presence of functional groups capable of attaching said ions to the beads.

20. A method for the separation and purification of enzymes, proteins, and nucleic acids which comprises contacting enzymes, proteins or nucleic acids with the porous beads of claim 17, said beads being further characterized by the presence of functional groups capable of attaching said enzymes, proteins or nucleic acids.

* * * * *